United States Patent [19]

Nakahara et al.

[11] Patent Number: 5,843,911
[45] Date of Patent: Dec. 1, 1998

[54] HYALURONIDASE INHIBITOR CONTAINING GOD-TYPE ELLAGITANNIN AS ACTIVE INGREDIENT

[75] Inventors: Koichi Nakahara; Katsuro Miyagawa; Tohru Kodama; Wataru Fujii, all of Osaka, Japan

[73] Assignee: Suntory Limited, Osaka, Japan

[21] Appl. No.: 600,111

[22] Filed: Feb. 12, 1996

[30]  Foreign Application Priority Data

Feb. 10, 1995  [JP]  Japan .................................. 7-045050
Sep. 1, 1995  [JP]  Japan .................................. 7-247025

[51] Int. Cl.⁶ .............................. A61K 7/48; A61K 35/78
[52] U.S. Cl. ............................................................... 514/38
[58] Field of Search ................................................ 514/38

[56]  References Cited

FOREIGN PATENT DOCUMENTS 0 657 169  6/1995  European Pat. Off. ....... A61K 35/78

OTHER PUBLICATIONS

European Search Report dated Nov. 26, 1996 for EP 96101936.1.
JP–A–06 192 144, Derwent abstract ( Jul. 12, 1994).
Kim, Youngsoo et al., "Inhibitory Effects of Herbal Medicines on Hyaluronidase Activity", *Kor. J. Pharmacogn.* 26(3):265–272 (Jan. 1, 1995).
JP–A–02 053 717, Derwent abstract (Feb. 22, 1990).
JP–A–03 145 430, Derwent abstract (Jun. 20, 1991).
JP–A–03 209 330, Derwent atstract (Sep. 12, 1991).
JP–A–63 115 807, Derwent abstract (May 20, 1988).
JP–A–62 249 907, Derwent abstract (Oct. 30, 1987).

*Primary Examiner*—Keith D. MacMillan
*Attorney, Agent, or Firm*—Cushman Darby & Cushman IP Group of Pillsbury, Madison & Sutro, LLP

[57]  ABSTRACT

Hyaluronidase inhibitor containing GOD-type ellagitannin as an active ingredient, as well as pharmaceuticals and cosmetics containing the inhibitor. The activity of hyaluronidase which hydrolyses hyaluronic acid can be inhibited without causing any toxicity to human, notably in the absence of irritation or any other adverse effects on the skin.

7 Claims, 3 Drawing Sheets

HYALURONIDASE INHIBITOR CONTAINING GOD-TYPE ELLAGITANNIN AS ACTIVE INGREDIENT

BACKGROUND OF THE INVENTION

This invention relates to a hyaluronidase inhibitor. More specifically, the invention relates to a hyaluronidase inhibitor containing GOD-type ellagitannin as an active ingredient, as well as pharmaceuticals and cosmetics containing said hyaluronidase inhibitor.

In order to keep the skin in a healthy condition, it is preferred to enhance the water retention of the skin per se. However, the water retention of the skin tends to decrease with age and the skin suffering from diseases such as inflammations is prone to decrease in water retention, so various methods are currently employed to enhance the moisture and water retaining effects of the skin. Even in the absence of these problems, enhancing the moisture and water retention of the skin contributes to moisturizing the skin, reducing roughness of skin and rendering it smooth. Hence, the enhancement of the skin's ability to retain moisture and water is one of the topics that are drawing particular attention today in the field of cosmetics.

Hyaluronic acid, which is distributed in skin's connective tissue and one of the components of the water retaining matrix, has drawn great interest as a substance responsible for the retention of moisture in the skin and it has been applied primarily to cosmetics and pharmaceuticals for external application. It has also been reported that the level of hyaluronic acid is low in the joint fluids of patients suffering from osteoarthritis or chronic rheumatism and an attempt is being made to apply hyaluronic acid to the palliative treatment of arthralgia or sharp pain in joints. Attention is also being drawn to the correlationship between the lower levels of hyaluronic acid in arterial walls and arteriosclerosis.

Besides the incorporation of hyaluronic acid, the presence of hyaluronidase which hydrolyses the hydraluronic acid inherent in the skin has recently drawn researchers' attention. The strategy they take is to inhibit the hyaluronidase which hydrolyses hyaluronic acid such that the action of the hyaluronic acid occurring in the skin by nature is maintained, whereby not only the moisture and water retention of the skin is enhanced as much as can be accomplished by the application of hyaluronic acid but also arthritis and other diseases due to the loss of hyaluronic acid are treated.

Thus, it has been desired to develop a material capable of inhibiting hyaluronidase without causing any toxicity to human, notably in the absence of irritation or any other adverse effects on the skin.

SUMMARY OF THE INVENTION

The present inventors conducted an extensive search for a natural substances generally recognized as safe, for example, food, food ingredient capable of excellent hyaluronidase inhibition. As a result, they found that the GOD-type ellagitannins present in Rosaceae and other plants had the desired hyaluronidase inhibiting activity. The present invention has been accomplished on the basis of this finding.

An object, therefore, of the invention is to provide a hyaluronidase inhibitor containing a GOD-type ellagitannin as an active ingredient.

Another object of the invention is to provide a pharmaceutical composition for external application that contains said hyaluronidase inhibitor.

A further object of the invention is to provide a cosmetic composition containing said hyaluronidase inhibitor.

DETAILED DESCRIPTION OF THE INVENTION

Figure 1:
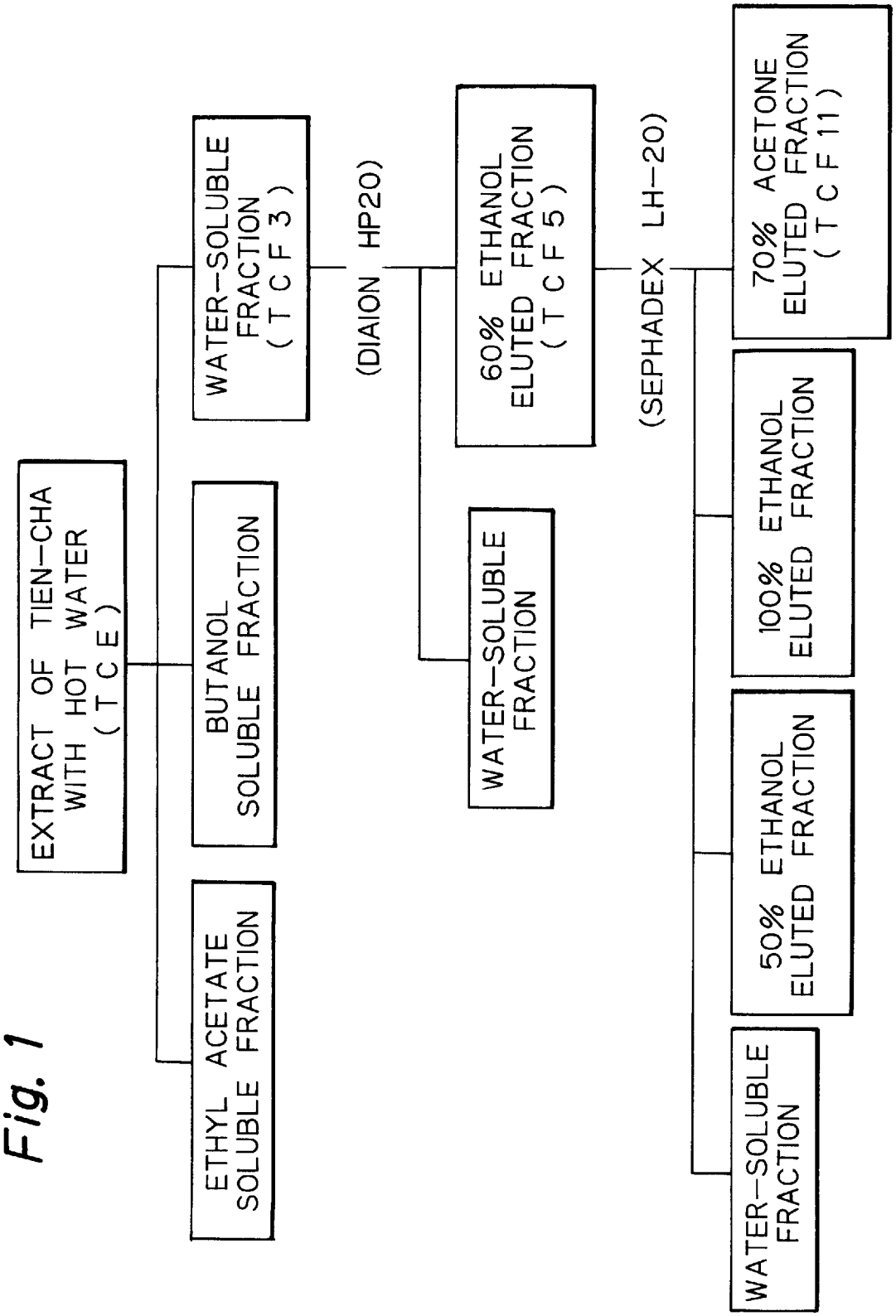
FIG. 1 shows a sequence for the production of a GOD-type ellagitannin from the extract of Tien-cha (*Rubus suavissimus* S. Lee.) with hot water in Preparation Example 1.

The GOD-type ellagitannin which is an active ingredient of the hyaluronidase inhibitor of the invention (said GOD-type ellagitannin is hereunder referred to as "GOD ellagitannin" for short) is a compound having a structural unit represented by the following formula (I):

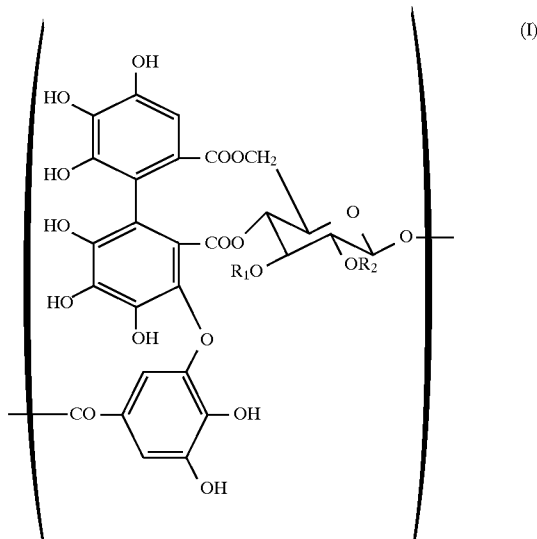

(where $R_1$ and $R_2$ each represents a hydrogen atom or a galloyl group or, when taken together, they represent a hexahydroxydiphenoyl group).

In addition to the saccharide structure, the structural unit contains a partial structure formed by ether bonding between the hexahydroxydiphenoyl group (hereunder sometimes abbreviated to D) and the galloyl group (hereunder sometimes abbreviated to G) as shown below:

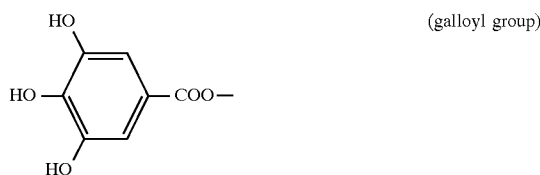

(galloyl group)

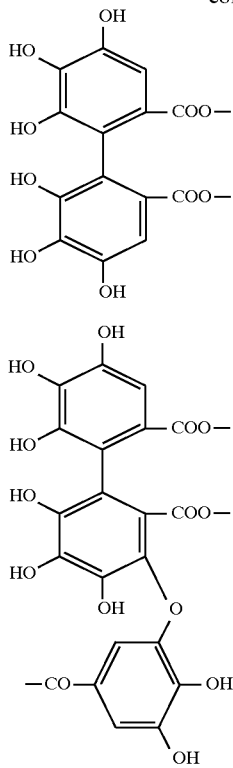

(hexahydroxydiphenoyl group)

(partial structure)

The oxygen in the ether bond in this partial structure is supplied from the G side and hence said partial structure is called a GOD type (G→O→D type, with O designating an oxygen atom).

The molecular weight of the GOD ellagitannin of the invention and the degree of its polymerization are not limited to any particular values as long as it has the above-defined structural unit. The molecular weights of Ellagitannin monomer and dimer from Tien-cha (*Rubus suavissims* S. Lee) extract wherein GOD ellagitannin contained were determined by FAB-MS using a Jeol JMS-HX110/110A tandem mass spectrometry system.

For estimation of molecular weight of polyphenol polymer, these compounds were methylated by diazomethane. The apparent molecular weight of the methylated active compounds from Tien-cha extract were determined by comparing the elution profiles on a TSK gel G3000H-XL (Tosoh Co., Tokyo, Japan) column (7.5×300 mm) in comparison to those of polystyrens of known molecular weight. Preferably, it has a molecular weight of no more than 20,000 with the degree of polymerization not more than 20. A particularly preferred GOD ellagitannin is represented by the following formula (II):

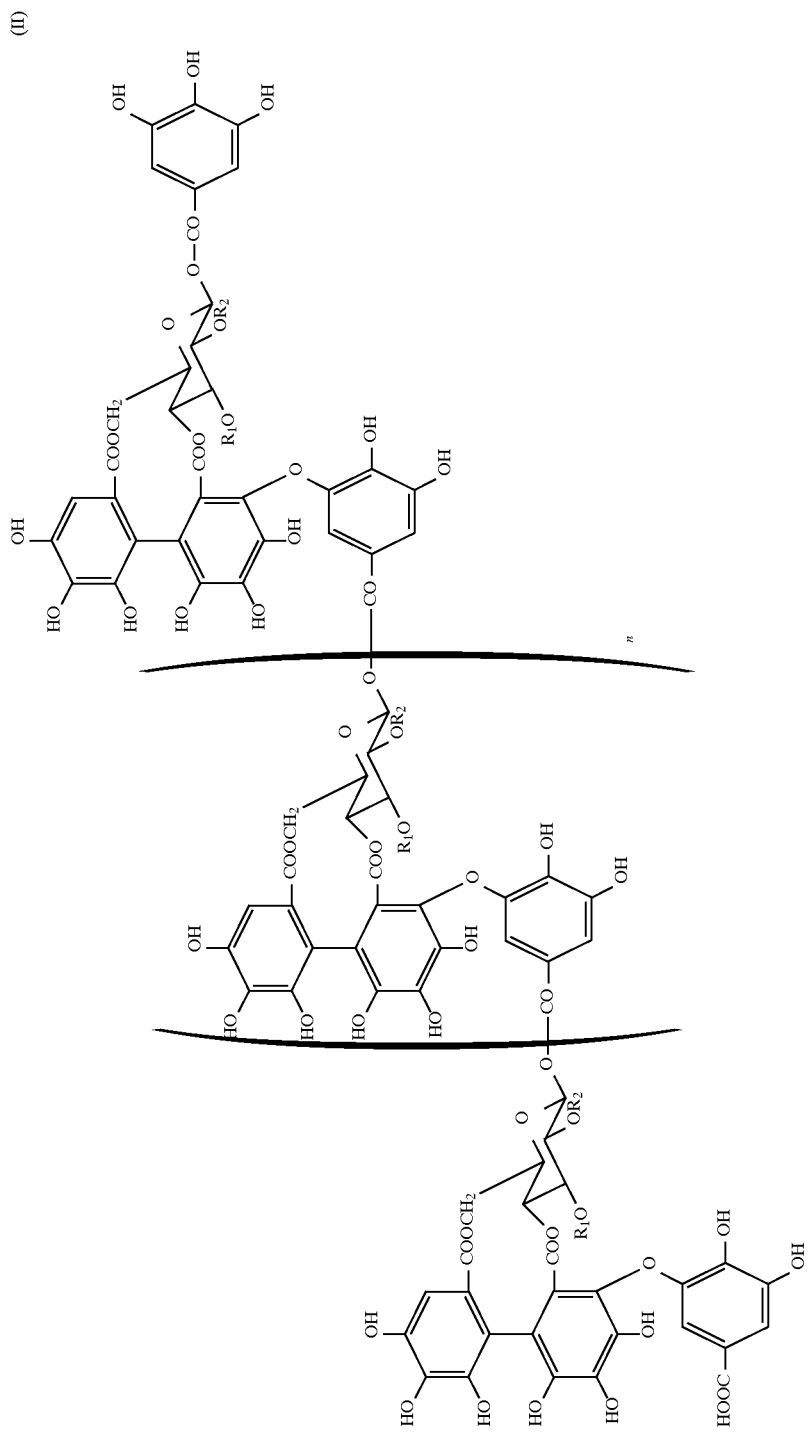

(where $R_1$ and $R_2$ have the same meanings as defined above; n is a number of from 0 to 20).

Another preferred GOD ellagitannin is represented by the following formula (III):

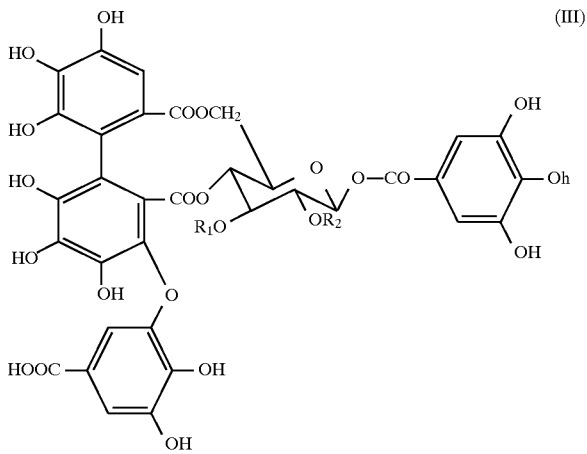

(where $R_1$ and $R_2$ have the same meanings as defined above).

The GOD ellagitannins mentioned above are known compounds and include the following: the GOD ellagitannin obtained from di-yu which is a crude drug prepared by drying the rhizome of *Sanguisorba officinalis* L. as described in Nonaka et al., J. C. S. Perkin I, 1067–1073 (1982); the GOD ellagitannin obtained from *R. henryi* BOUL as described in Yoshida et al., Chem. Pharm. Bull. 40(8), 1997–2001 (1992); and the GOD ellagitannin obtained from rubus such as *R. crataegifolius* BUNGE, *R. parvifolius* L., *R. palmatus* THUNB, *R. sieboldii* BLUME, *R. corchorifolius* L., *R. palmatus* THUNB. var *coptophyllus* KUNZE, *R. idaeus* L., *R. mesogeanus* FOCKE, *R. phoenicolasius* MAXIM., *R. calycinoides* HAYATO, *R. lambertianus* SERINGE, *S. tenuifolia* var *parviflora* and *Rubus chingii* as described in Tanaka et al., Chem. Pharm. Bull. 41(7), 1214–1220 (1993). These GOD ellagitannins are useful as an active ingredient in the hyaluronidase inhibitor of the invention.

The GOD ellagitannins that can be used in the invention are by no means limited to those described in the references listed above and also useful are those GOD ellagitannins that were extracted and purified from other plants that contain the compound of interest.

The plants from which the GOD ellagitannin can be extracted are not limited to any particular types and, besides the plants used as starting materials in the references listed above, other plants of the rose family (Rosaceae) may be employed, among which the following are particularly mentioned: *Rubus microphyllus, R. koehncanus, R. trifidus, R. medius, R. acuminatus, R. ellipticus, R. multibureatus, R. coreanus, R. foliosus, R. parvifolius, Rubus suavissimus* S. Lee., *Rubus babae* Naruhashi, *Rubus fruticosus* L., *Rubus hiraseanus* Makino, *Rubus hirsutus* Thunb., *Rubus masakii* Naruhashi, *Rubus medius* O.Ktze., *Rubus nigakuma* Oka et Naruhashi, *Rubus nikail* Ohwi, *Rubus ohmineanus* Koidz., *Rubus pedatus* Smith, *Rubus pseudochingii* Naruhashi, *Rubus tawadanus* Koidz., *Rubus toyorensis* Koidz., *Rubus trifidus* Thunb. ex Murrey, *Rubus utchinensis* Koidz., *Rubus yenoshimanu* Koidz., and *Sanguisorba tenuifolia* Fisch. var. alba Trautv. et Meyer.

To extract GOD ellagitannins from the plants mentioned above, various solvents may be used and they include water, alcohols such as methanol and ethanol, and other water miscible organic solvents including ketones such as acetone. These solvents may be used individually or in admixtures. From safety and operational viewpoints, the use of water, alcohols and mixtures thereof is preferred.

The ratio between the plant and the extracting solvent is in no way limited but the solvent is preferably used in amounts 2–1,000 times as much as the plant, with 5–100 times being particularly preferred from the viewpoints of ease of extraction and its efficiency. The extraction temperature is conveniently selected from the range of room temperature to the boiling point of the solvent at atmospheric pressure. The extraction time varies with the extraction temperature and other factors but is preferably selected from several seconds to two days. Any part of the plant may be extracted including leaves, stems and roots.

If desired, plants containing the GOD ellagitannin may be shredded and the shredded plants may be used for extraction.

The plant extracts thus prepared may be worked up to GOD ellagitannins of higher purity by subjecting them to various purification techniques such as treatment with adsorbents, membrane separation and solvent fractionation.

To purify the active ingredient of the plant extracts, the plant extracts may be treated by further extraction with any solvents that are not highly miscible with the GOD ellagitannin and which are separable from water; preferred solvents include butanol, ethyl acetate and methyl acetate. Another workup procedure that can be adopted is fractionation by molecular weight using an ultrafiltration (UF) membrane.

Alternatively, the plant extract or products thereof by fractionation with solvents may be subjected to adsorption column chromatography and eluted with one or more solvents to provide GOD ellagitannins of higher purity.

Adsorptive partitioning by adsorption column chromatography may proceed as follows: the plant extract or products of its fractionation with solvents are dissolved in a small amount of a solvent such as water, methanol or ethanol or a mixture thereof; the solution is adsorbed on an adsorbent in column such as Sephadex LH-20 (Pharmacia, Sweden), Diaion HP20 (Mitsubishi Kasei Corp.), Develosil ODS (Nomura Chemical Co.), Sepabeads HP1MG (Mitsubishi Kasei Corp.) or Toyopearl HW40F (Tosoh Co.), washed thoroughly with water, and eluted with a hydrophilic solvent such as methanol, ethanol or acetone or a mixture thereof. GOD ellagitannins of much higher purity can be obtained by tandem adsorption column chromatography.

The thus prepared GOD ellagitannins may be formulated as the hyaluronidase inhibitor of the invention either as such or by combining them with known pharmaceutical vehicles such as waxes, lanolin, surfactants and cetanol.

The hyaluronidase inhibitor of the invention may be used as a pharmaceutical, especially as a parenteral one such as an injection, a suppository or a drug for external application. A pharmaceutical vehicles that are commonly used in accordance with these dosage forms may be employed without any particular limitations.

If the hyaluronidase inhibitor of the invention is formulated for external application such as in the form of an ointment, a cream, a solution or a plaster, it can effectively be used in the treatment of rough skin. For the treatment of osteoarthritis, and chronic rheumarthritis, or relieving sharp pain, the inhibitor may be administered as an injection.

If the hyaluronidase inhibitor of the invention is to be used as a pharmaceutical drug, the dosage of the GOD ellagitannin should be determined as appropriate for the purity of the GOD ellagitannin, the design of formulation, the age of the patient or the severity of the disease.

The hyaluronidase inhibitor of the invention will exhibit superior effects when it is used as cosmetics or cosmetic additives, and particularly good results are assured when it is used as skin care products. The hyaluronidase inhibitor may be used as a humectant.

The cosmetics of the invention can be included with the hyaluronidase inhibitor of the invention which is used as a cosmetic additive. The cosmetics included the hyaluronidase inhibitor of the invention may incorporate generally cosmetic vehicles and other ingredients including oils such as vegetable oils, waxes such as lanolin and beeswax, hydrocarbons, fatty acids, higher alcohols, esters, various surfactants, coloring agent, flavoring agents, vitamins, plant or animal extracts, uv absorbers, antioxides, antiseptics and sterilizers. The cosmetics of the invention can be provided with even better efficacy by incorporating other anti-inflammatory or antiallergic cosmetic ingredients such as licorice extracts (in particular, glycyrrhetic acid), hydrochloric acid diphenhydramine, azulene, dl-α-tocopherol or derivatives thereof, or vitamins $B_2$ and $B_6$.

The hyaluronidase inhibitor of the invention, when incorporated into cosmetics, will inhibit the hydrolysis of hyaluronic acid in the skin, thereby imparting indirect skin moisturing and reducing roughness effects.

Cosmetics having further enhanced moisturizing effect can be produced by using the hyaluronidase inhibitor of the invention in combination with hyaluronic acid. The same result can be attained by incorporating other skin moisturing and reducing roughness cosmetic vehicles and other ingredients such as elastin, collagen, lecithin, squalene, placental liquids (as extracted from the placenta), glycerins, glycols, fermentation metabolites, solutions of culture of lactobacilli, vitamins A and C, sodium chondroitin sulfate, 2-pyrrolidone-5-carboxylic acid sodium (PCA-Na) and plant polysaccharides such as the one contained in the mucus of phipogonis tubers.

The hyaluronidase inhibitor of the invention can be incorporated in various cosmetic formulations such as lotions, creams, emulsions, foundations, lipsticks, hair care products, hair tonics and hair nourishers, toothpastes, mouth washers, shampoos, body shampoos, rinses bath salts and bath oils.

The GOD ellagitannin which is the active ingredient of the hyaluronidase inhibitor of the invention is also contained in Tien-cha (*Rubus suavissimus* S. Lee) which has been taken habitually as tea in the southern part of People's Republic of China and, hence, it has been recognized as safe at all. When it is to be incorporated in cosmetics, color considerations dictate that its concentration should desirably be adjusted to range from 0.0001 to 5.0% on the basis of the GOD ellagitannin in a pure form.

The GOD ellagitannin which is the active ingredient in the hyaluronidase inhibitor of the invention has an efficient hyaluronidase inhibiting activity and is effective for various purposes, such as inhibiting the reduction in the hyaluronic acid content of the skin, arterial walls and cavities in joints, enhancing the moisture retention, reducing roughness of skin and smooth softness of the skin, preventing arteriosclerosis the incidence of which tends to increase with age, and ameliorating arthritis.

Notably, the inhibitor has skin moisturizing, reducing roughness of skin and smoothing effects and yet it causes no toxicity to human without irritating or otherwise adversely affecting the skin. Hence, the inhibitor is optimal for use as an ingredient of cosmetics.

The following preparation examples for the GOD ellagitannin and the associated working examples are provided for the purpose of further illustrating the present invention but are in no way to be taken as limiting.

Preparation Example 1

Preparing GOD ellagitannin from Tien-cha (1):

A hundred grams of Tien-cha leaves were put into a 3,000-ml conical flask. Following the addition of hot water (1,000 ml), the tea leaves were subjected to extraction in a boiling water bath. The extract was filtered and the filtrate was freeze-dried to yield 32 g of a Tien-cha extract (which is hereunder referred to as TCE).

A portion (23 g) of the Tien-cha extract was dissolved in 2 L of water and subjected to solvent fractionation with the same amounts of ethyl acetate and n-butanol in that order to yield 15 g of a water-soluble fraction (which is hereunder referred to as TCF-3). The fraction was dissolved in 500 ml of water, adsorbed on a column (4 cmφ×32 cm) of Diaion HP-20 (Mitsubishi Kasei Corp.), washed with 2 L of water and eluted with 2 L of 60 vol % ethanol in water to yield 5.6 g of 60% ethanol eluted fraction (which is hereunder referred to as TCF5). The fraction was dissolved in 100 ml of water-ethanol (1:1 v/v), adsorbed on a column (4 cmφ×30 cm) of Sephadex LH-20 (Pharmacia, Sweden), washed with 1 L of water, eluted with 1 L each of 50 vol % ethanol in water and ethanol in that order, and further eluted with 70 vol % acetone in water to yield 1.7 g of a 70% acetone eluted fraction (which is hereunder referred to as TCF11). These procedures of preparation and purification are shown schematically in FIG. 1.

Figure 2:
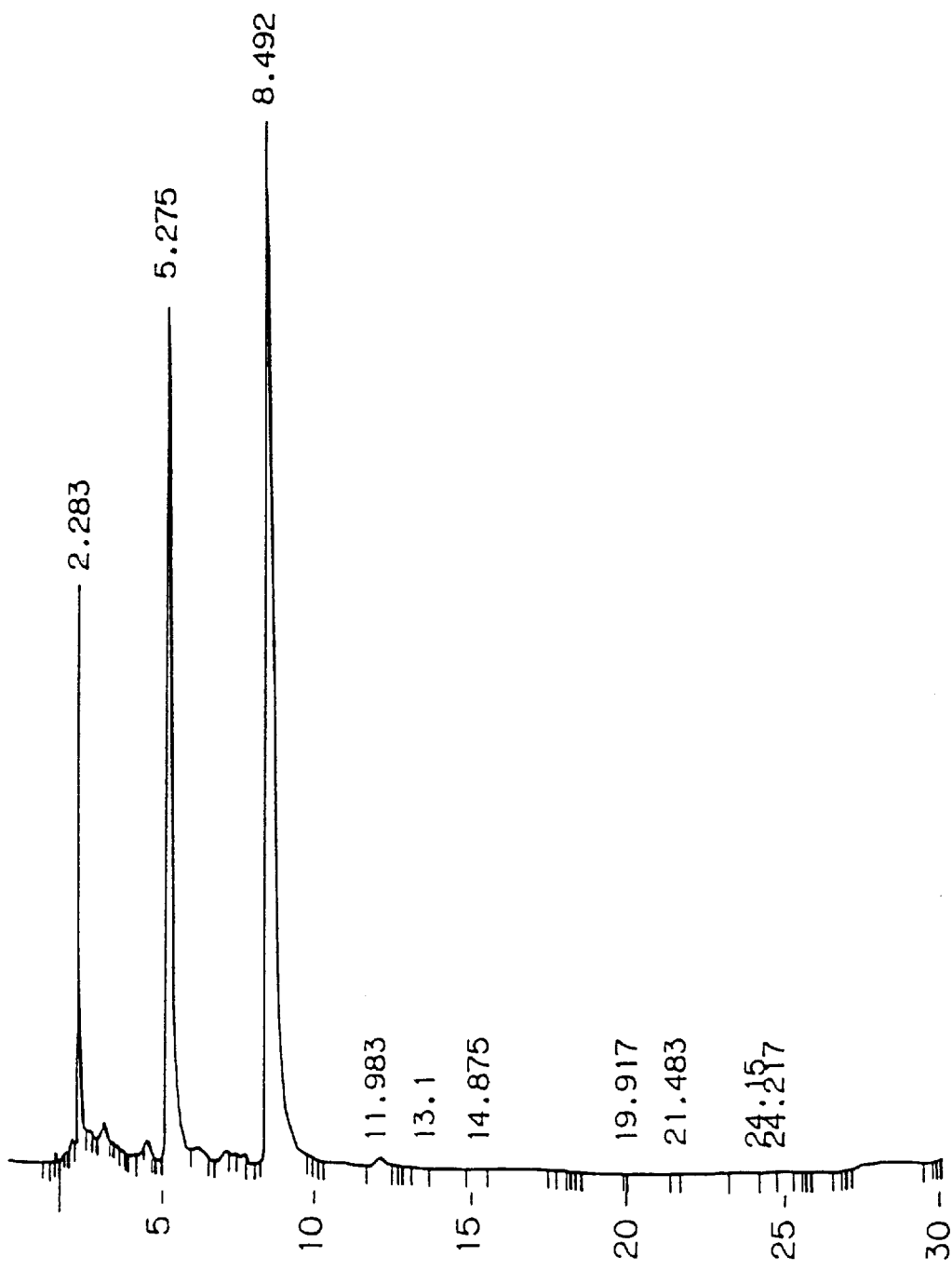
FIG. 2 shows the results of HPLC analysis on the hydrolyzate of the GOD-type ellagitannin produced in Preparation Example 1.

A portion (5 mg) of TCF11 (70% acetone eluted fraction) was dissolved in 2 ml of 1N HCl, heated at 100° C. for 2 h and subjected to three extractions with 2 ml of ethyl acetate. The extract was analyzed by HPLC and the results are shown in FIG. 2. Three peaks appeared at retention times of 5.275 min (sanguisorbic acid dilactone, GOD), 2.283 min (gallic acid, G) and 8.492 min (ellagic acid, D). Thus, the formation of GOD-type ellagitannin was verified. TCF11 contained the GOD ellagitannin at a concentration of 90%.

The conditions for the HPLC analysis were as follows: the column was packed with Develosil ODS-5 (4.5 mm×150 mm; product of Nomura Chemical Co.), which was eluted with a solvent system consisting of 0.05M monopotassium phosphate, 0.05M phosphoric acid, ethanol and ethyl acetate (40:40:15:5 v/v), with uv detection conducted at 280 nm.

Preparation Example 2

Preparing GOD ellagitannin from Tien-cha (2):

Ten grams of the extract of Tien-cha with hot water was dissolved in 1 L of water and subjected to solvent fractionation with the same amounts of ethyl acetate and n-butanol in that order to yield 6.58 g of a water-soluble fraction. A portion (1 g) of the fraction was dissolved in 5 ml of water, adsorbed on a column (4 cmφ×30 cm) of Develosil ODS-10 (Nomura Chemical Co), washed with 2 L of water, and eluted with 2 L of 20 vol % ethanol in water to yield 0.36 g of a 20% ethanol eluted fraction.

The formation of a GOD ellagitannin in the 20% ethanol eluted fraction from Develosil ODS-10 was verified by the same method as in Preparation Example 1.

Preparation Example 3

Figure 3:
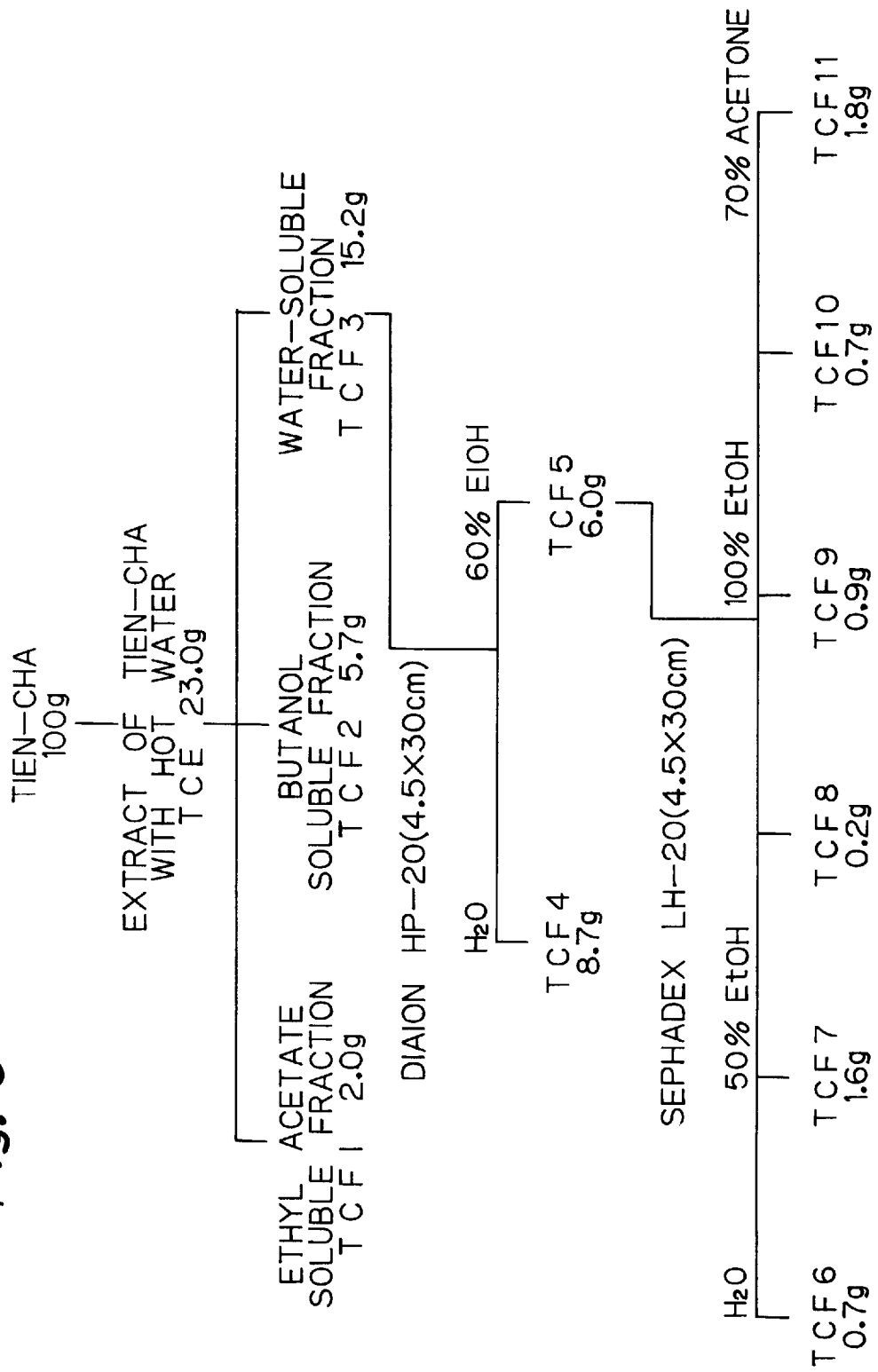
FIG. 3 shows a sequence for the production of a GOD-type ellagitannin from the extract of Tien-cha with hot water in Preparation Example 3.

Preparing GOD ellagitannin from Tien-cha (3):

Tien-cha leaves were subjected to extraction with hot water as in Preparation Example 1. A portion (23 g) of the extract was fractionated as in Preparation Example 1 by the procedures illustrated in FIG. 3 to yield four fractions, TCE, TCF3, TCF5 and TCF11.

Example 1

Assay for the hyaluronidase inhibiting activity:

The GOD ellagitannins prepared in Preparation Examples 1 and 2 were assayed for their hyaluronidase inhibiting activity by the following method of measurement. The results are shown in Table 1.

(Method of measuring the hyaluronidase inhibiting activity)

Using a bovine testis-derived hyaluronidase (Type IV of Sigma), the action of compound 48/80 in inhibiting the activation stage of an inactivated enzyme was evaluated. The enzymatic activity was measured by colorimetric determination with $A_{585}$ of the increase in the reducing power of a tetrasaccharide that was generated by hydrolysis of hyaluronic acid and which had N-acetylhexosamine at the reducing terminus (see Y. Maeda et al., SHOKUEISHI, Vol. 31, pp. 233–237, 1990).

Stated more specifically, a suitable amount of a test sample was dissolved in 100 μl of a 0.1M acetate buffer solution (pH 4.0) and the solution was pipetted into a test tube. Following the addition of 0.10 mg (100 NF units) of the enzyme dissolved in 50 μl of the same buffer solution, the mixture was incubated at 37° C. for 20 min. Subsequently, 50 μg of compound 48/80 dissolved in 100 μl of the same buffer solution was added and the mixture was incubated at 37° C. for 20 min.

Thereafter, 200 μg of sodium hyaluronate derived from a microorganism dissolved in 250 μl of the same buffer solution was added and the mixture was incubated at 37° C. for 40 min. Finally, 100 μl of 0.4N NaOH was added and, after cooling with ice, 100 μl of a borate buffer solution (pH 9.10) was added and the mixture was boiled for 3 min; after cooling with ice, 3 ml of a p-dimethylaminobenzaldehyde solution was added and the mixture was incubated for 20 min at 37° C. before $A_{585}$ measurement was conducted.

In place of the sample solution, 0.1M acetate buffer solution (pH 4.0) was used to prepare a control. A blank was prepared for each of the sample solution and the control by substituting 0.1M acetate buffer solution (pH 4.0) for the enzyme solution. The hyaluronidase inhibiting activity of the sample solution was expressed by percent inhibition as determined from the following equation:

$$\text{percent inhibition} = \frac{(A-B)-(C-D)}{(A-B)} \times 100$$

where

A: $A_{585}$ of the control solution
B: $A_{585}$ of the blank for the control solution
C: $A_{585}$ of the sample solution
D: $A_{585}$ of the blank for the sample solution.

TABLE 1

| Test Sample | Hyaluronidase inhibiting activity, $IC_{50}$ (ppm) |
|---|---|
| Sodium cromoglycate | 140 |
| Tien-cha extract with hot water (Preparation Example 1) | 140 |
| 60% Ethanol eluted fraction from Diaion HP-20 (Preparation Example 1) | 45 |
| 70% Acetone eluted fraction from Sephadex LH-20 (Preparation Example 1) | 25 |
| Tien-cha extract with hot water (Preparation Example 2) | 140 |
| 20% Ethanol eluted fraction from Develosil ODS-10 (Preparation Example 2) | 40 |

Example 2

Emollient lotion:

An emollient lotion was prepared from the following formulation.

| Formula | Content (%) |
|---|---|
| Stearic acid | 2.0 |
| Cetyl alcohol | 1.5 |
| Petrolatum | 3.0 |
| Lanolin alcohol | 2.0 |
| Liquid paraffin | 10.0 |
| Polyoxyethylene monooleic acid ester (10 E.O.) | 2.0 |
| Propylene glycol | 4.8 |
| Glycerin | 3.0 |
| Triethanolamine | 1.0 |
| Sodium hyaluronate | 0.1 |
| GOD ellagitannin* | 0.1 |
| Flavoring agent | 0.1 |
| Purified water | 70.4 |

*GOD ellagitannin: 20% ethanol eluted fraction from develosil ODS-10 in Preparation Example 2

Example 3

Lotion:

Lotion was prepared from the following formulations by the method also described below.

| | Content (%) |
|---|---|
| Formula (A) | |
| Glycerin | 8.0 |
| Sorbitol | 6.0 |
| GOD ellagitannin* | 0.2 |
| Sodium methacrylicate | 0.1 |
| Citric acid | 0.04 |
| Sodium citrate | 0.16 |
| Purified water | bal. |
| Formula (B) | |
| Ethanol | 10.0 |
| POE (60) hardened castor oil | 0.5 |
| Purified lecithin | 0.04 |
| Methyl paraben | 0.1 |
| Flavoring agent | 0.06 |

*GOD ellagitannin: 20% ethanol eluted fraction from Develosil ODS-10 in Preparation Example 2

(Method of Preparation)

Formulation (A) and (B) were each processed into a uniform solution and the solution of (B) was added to that of (A), thereby yielding lotion.

Example 4

Emollient cream:

Emollient cream was prepared from the following formulations by the method also described below.

|  | Content (%) |
|---|---|
| Formula (A) | |
| Propylene glycol | 8.0 |
| Glycerin | 4.0 |
| Triethanolamine | 1.0 |
| GOD ellagitannin* | 0.5 |
| Purified water | 57.0 |
| Formula (B) | |
| Beeswax | 2.0 |
| Stearyl alcohol | 5.0 |
| Stearic acid | 8.0 |
| Squalane | 10.0 |
| Self-emulsifying propylene glycol monostearate | 3.0 |
| Polyoxethylene cetyl ether (20 E.O.) | 1.0 |
| Flavoring agent | 0.5 |
| Antiseptic acid antioxidant | q.s. |

*GOD ellagitannin: 20% ethanol eluted fraction from Develosil ODS-10 in Preparation Example 2

(Method of Preparation)

Propylene glycol, glycerin and triethanolamine were added to purified water and the mixture was heated at 70° C. The other ingredients were added and the mixture was heated to melt at 70° C. The resulting oil phase was added to the aqueous phase and reaction was performed. The reaction mixture was emulsified uniformly with a homomixer and thereafter cooled to 30° C. with a heat exchanger.

Example 5

Drug for external application (ointment):

An ointment was prepared according to the following formulation.

| Formula | Content (%) |
|---|---|
| GOD ellagitannin* | 5.0 |
| Petrolatum | 90.0 |
| Isopropyl myristate | 5.0 |

*GOD ellagitannin: 20% ethanol eluted fraction from Develosil ODS-10 in Preparation Example 2

What is claimed is:

1. A hyaluronidase inhibitor comprising a GOD-type ellagitannin represented by the formula:

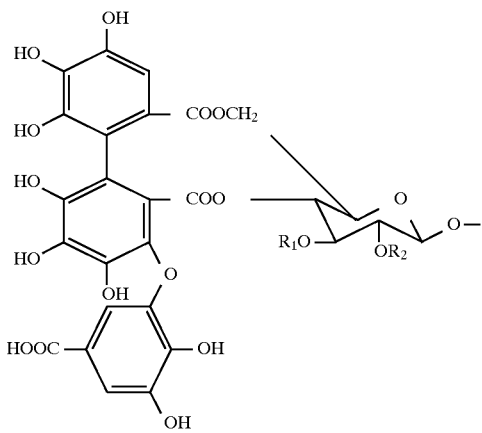

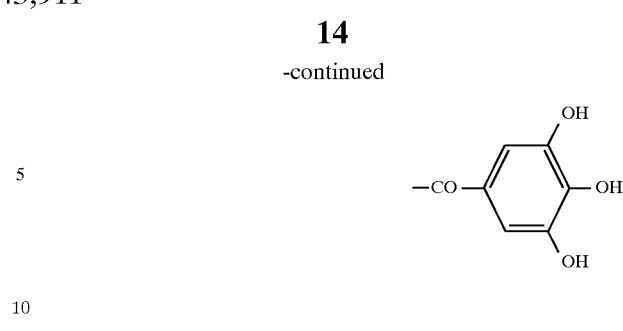

wherein $R_1$ and $R_2$ each represents a hydrogen atom or a galloyl group or, when taken together they represent a hexahydroxydiphenoyl group, and a pharmaceutically acceptable carrier.

2. A hyaluronidase inhibitor according to claim 1, wherein the GOD-type ellagitannin is an extract from a Rubus or Rosa.

3. A hyaluronidase inhibitor according to claim 2, wherein the Rubus or Rosa is selected from the group consisting of *Rubus suavissimus* S.Lee, *Rubus chingii*, *Rubus coreanus*, *Rosa henryi* BOUL., *Rubus crataegifolius* BUNGE, *Rubus parvifolius* L., *Rubus palmatus* THUNB., *Rubus sieboldii* BLUME, *Rubus corchorifolius* L., *Rubus palmatus* THUNB. var *coptophyllus* KUNZE, *Rubus idaeus* L., *Rubus mesogeanus* FOCKE, *Rubus phoenicolasius* MAXIM., *Rubus calycinoides* HAYATO, *Rubus lambertianus* SERINGE, *Rubus babae* Naruhashi, *Rubus fruticosus* L., *Rubus hiraseanus* Makino, *Rubus hirsutus* Thunb., *Rubus masakii* Naruhashi, *Rubus medius* O.Ktze., *Rubus nigakuma* Oka et Naruhashi, *Rubus nikaii* Ohwi, *Rubus ohmineanus* Koidz., *Rubus pedatus* Smith, *Rubus pseudochingii* Naruhashi, *Rubus tawadanus* Koidz., *Rubus toyorensis* Koidz., *Rubus trifidus* Thunb. ex Murrey, *Rubus utchinensis* Koidz., and *Rubus yenoshimanus* Koidz.

4. A pharmaceutical composition for external application which comprises the hyaluronidase inhibitor of claim 1 and a pharmaceutically acceptable vehicle.

5. A cosmetic composition comprising the hyaluronidase inhibitor of claim 1 and a cosmetically acceptable vehicle.

6. A humectant composition comprising the hyaluronidase inhibitor of claim 1 and an acceptable humectant vehicle.

7. A method of treating inflamed tissues by administering an anti-inflammatory pharmaceutical composition in a pharmaceutically effective amount to tissues in need of such treatment, said composition comprising the hyaluronidase inhibitor of claim 1 and a pharmaceutically acceptable vehicle.

* * * * *